US006536944B1

(12) United States Patent
Archibald et al.

(10) Patent No.: US 6,536,944 B1
(45) Date of Patent: Mar. 25, 2003

(54) PARALLEL SCREEN FOR RAPID THERMAL CHARACTERIZATION OF MATERIALS

(75) Inventors: William B. Archibald, Hillsborough, CA (US); Marc Hornbostel, Palo Alto, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/414,744

(22) Filed: Oct. 8, 1999

Related U.S. Application Data

(63) Continuation-in-part of application No. PCT/US99/07358, filed on Apr. 1, 1999, which is a continuation-in-part of application No. 09/227,558, filed on Jan. 8, 1999, which is a continuation-in-part of application No. 08/898,715, filed on Jul. 22, 1997, now Pat. No. 6,030,917.

(60) Provisional application No. 60/050,949, filed on Jun. 13, 1997, provisional application No. 60/035,366, filed on Jan. 10, 1997, provisional application No. 60/048,987, filed on Jun. 9, 1997, provisional application No. 60/035,202, filed on Jan. 10, 1997, provisional application No. 60/028,106, filed on Oct. 9, 1996, provisional application No. 60/029,255, filed on Oct. 25, 1996, and provisional application No. 60/028,105, filed on Oct. 9, 1996.

(51) Int. Cl.$^7$ .............................................. G01N 25/04
(52) U.S. Cl. ........................ 374/20; 436/147; 436/181; 219/497; 250/341.6
(58) Field of Search .............................. 374/16, 17, 18, 374/19, 20, 33, 34, 36, 1; 250/341.1, 341.6, 341.8; 219/497; 436/181, 147

(56) References Cited

U.S. PATENT DOCUMENTS

| | | | | |
|---|---|---|---|---|
| 1,259,363 A | * | 3/1918 | Chubb ........................ | 374/16 |
| 2,986,028 A | * | 5/1961 | Shawhan ..................... | 374/33 |
| 3,501,580 A | * | 3/1970 | Stingele ...................... | 374/17 |
| 3,969,013 A | * | 7/1976 | Poty et al. ................... | 374/17 |
| 4,690,569 A | * | 9/1987 | Veitch ........................ | 374/121 |
| 4,897,149 A | * | 1/1990 | Suzuki et al. ............... | 428/698 |

(List continued on next page.)

FOREIGN PATENT DOCUMENTS

| | | | |
|---|---|---|---|
| DE | 96 32 779 A1 | 2/1998 | |
| EP | 0 535 881 A1 | 4/1993 | |
| GB | 2 202 941 A * | 10/1998 | .................. 374/16 |
| JP | 2-208547 A * | 8/1990 | .................. 374/16 |
| JP | 3-186747 A * | 8/1991 | .................. 374/16 |
| WO | 97/32208 | 9/1997 | |
| WO | 98/07026 | 2/1998 | |
| WO | 99/34206 | 7/1999 | |

OTHER PUBLICATIONS

Model 992 Industrial Dew Point Hygrometer, Technical Data Sheet 992B3, Cambridge Systems, Feb. 1996.*

Dersch et al., "Optical approach to thermopower and conductively measurements in thin–film semiconductors", Applied Physics Letters, vol. 45, No. 3, Aug. 1, 1984, 272–274.

Georgiades et al., "IR Emission Analysis of Temperature Profiles in Pt/SiO$_2$ Catalysts During Exothermic Reactions", Chem. Int. Ed. Engl. 26, No. 10, 1987, 1042–1043. (No Month).

Hardisty et al., "Thermal Imaging in Electronics and Rotating Machinery", 32$^{nd}$ Annual British Conf. on Non–Destructive Testing, Sep. 14–16, 1993, pp. 73–78, vol. 36, No. 2, Feb. 1994, British Journal of NDT.

(List continued on next page.)

Primary Examiner—Diego Gutierrez
Assistant Examiner—Stanley J. Pruchnic, Jr.
(74) Attorney, Agent, or Firm—Dobrusin Thennisch PC

(57) ABSTRACT

A method and apparatus for high-throughput determination of phase change points of combinatorial libraries of metal alloys uses an infrared camera to monitor temperature-dependent changes in emissivity/reflectivity of the alloys. An infrared focal plane array monitors the emissivity/reflectivity changes over time, and the intensity of each heated member over time is correlated with temperature to detect the phase change points of the members.

44 Claims, 3 Drawing Sheets

U.S. PATENT DOCUMENTS

| | | | |
|---|---|---|---|
| 4,998,284 A | | 3/1991 | Bacus et al. ............... 382/133 |
| 5,032,727 A | * | 7/1991 | Cox, Jr. et al. ............ 250/330 |
| 5,127,063 A | | 6/1992 | Nishiya et al. ............ 382/141 |
| 5,265,957 A | * | 11/1993 | Moslehi et al. ............... 374/1 |
| 5,288,148 A | * | 2/1994 | Rahimzadeh ............... 374/19 |
| 5,356,756 A | * | 10/1994 | Cavicchi et al. ............ 430/315 |
| 5,549,996 A | | 8/1996 | Bollen ........................ 430/21 |
| 5,553,939 A | * | 9/1996 | Dilhac et al. .................. 374/1 |
| 5,631,734 A | | 5/1997 | Stern et al. ................ 356/317 |
| 5,653,539 A | * | 8/1997 | Rosengaus ................ 436/147 |
| 5,758,968 A | * | 6/1998 | Diebold ....................... 374/17 |
| 5,776,359 A | | 7/1998 | Schultz et al. ............. 423/263 |
| 5,856,101 A | | 1/1999 | Hubbell et al. ................ 435/6 |
| 5,874,667 A | * | 2/1999 | Kasman ....................... 374/16 |
| 5,974,164 A | | 10/1999 | Chee .......................... 382/129 |
| 6,022,141 A | * | 2/2000 | Bass .......................... 436/147 |
| 6,025,601 A | | 2/2000 | Trulson et al. ............ 250/461.2 |
| 6,063,633 A | * | 5/2000 | Willson, III ............... 436/147 |
| 6,333,196 B1 | * | 12/2001 | Willson, III ............... 436/147 |

OTHER PUBLICATIONS

Holzwarth et al., "Detection of Catalytic Activity in Combinatorial Libraries of Heterogeneous Catalysts by IR Thermography", Angew. Chem. Int. Ed. 37 No. 19, pp. 2644–2647, Oct. 1998.

Lewis et al., "Fourier Transform Spectroscopic Imaging Using an Infrared Focal–Plane Array Detector", Anal. Chem. 1995, 67, pp. 3377–3381. (No Month).

Moates et al., "Infrared Thermographic Screening of Combinatorial Libraries of Heterongeneous Catalysts", Screening Catalyst Activity, 8/97, pp. 683–686.

Moates, et al., "Infrared Thermographic Screening of Combinatorial Libraries of Heterogeneous Catalysts," *Ind. Eng. Chem. Res.*, 1996, vol. 35, No. 12, pp. 4801–4803, Dec. 1996.

Pawlicki et al., "Spatial Effects on Supported Catalysts", Chem. Eng. Progress, 2/87, pp. 40–45.

Reddington et al., "Combinatorial Electrochemistry: A Highly Parallel, Optical Screening Method for Discovery of Better Electrocatalysts", Science vol. 280, Jun. 12, 1998, pp. 1735–1737.

Taylor et al., "Thermographic Selection of Effective Catalysts from an Encoded Polymer–Bound Library", Science, vol. 280, Apr. 10, 1998, pp. 267–270.

PCT International Search Report, PCT–US99/07358, Aug. 16, 1999.

* cited by examiner

PARALLEL SCREEN FOR RAPID THERMAL CHARACTERIZATION OF MATERIALS

CROSS-REFERENCE TO RELATED APPLICATIONS

This application is a continuation-in-part and claims priority to international application PCT/US99/07358, which is a continuation-in-part of commonly assigned, co-pending U.S. patent application Ser. No. 09/227,558, filed Jan. 8, 1999, which is a continuation-in-part of U.S. application Ser. No. 08/898,715, filed Jul. 22, 1997, and U.S. Provisional Application No. 60/050,949, filed Jun. 13, 1997; No. 60/028,106, filed Oct. 9, 1996; No. 60/029,255, filed Oct. 25, 1996; No. 60/035,366, filed Jan. 10, 1997; No. 60/048,987, filed Jun. 9, 1997; No. 60/028,105, filed Oct. 9, 1996; and No. 60/035,202, filed Jan. 10, 1997. Each of the foregoing applications is incorporated herein by reference in its entirety and is the basis of a claim for priority under 35 U.S.C. Section 119 or 120.

TECHNICAL FIELD

The present invention is directed to combinatorial techniques for characterizing materials, and more particularly to a parallel screen for determining the thermal characteristics of materials by monitoring changes in radiation intensity from members of a combinatorial library as a function of temperature.

BACKGROUND ART

In discovering new materials, the temperature of a material phase change (e.g. melting point) provides important information regarding a particular material. One possible approach for determining such temperatures is to measure the difference between the temperature of the unknown member and a reference member, as in differential scanning calorimetry (DSC) and differential thermal analysis (DTA). Another approach is to monitor changes in the reflectivity or emissivity of the unknown member as a function of temperature. Currently, there is a need for a rapid, high throughput screen that can determine the thermal characteristics of members of a combinatorial library over a large temperature range.

SUMMARY OF THE INVENTION

Accordingly, the invention applies combinatorial materials science techniques in a high-throughput screen for measuring the phase change temperatures of combinatorial libraries of materials. Generally, the invention is directed to correlating the intensity of the radiation emitting from a member with its temperature to obtain its thermal characteristics, and more particularly to correlating the radiation intensity of each member versus time and correlating the temperature of each member versus time to link the member's radiation intensity with its temperature. The invention may include using a detector, such as an infrared camera, to measure the phase change temperature (e.g. melting point) of a plurality of materials on a substrate by, for example, monitoring changes in the radiation, such as the reflectance or emissivity, of a member. In one embodiment, the infrared camera compares the radiation from a substrate to the radiation from a member as a function of temperature. The phase change temperature of the member is obtained by monitoring changes in the ratio between the two radiations as a function of temperature.

DETAILED DESCRIPTION OF THE PREFERRED EMBODIMENTS

Figure 1:
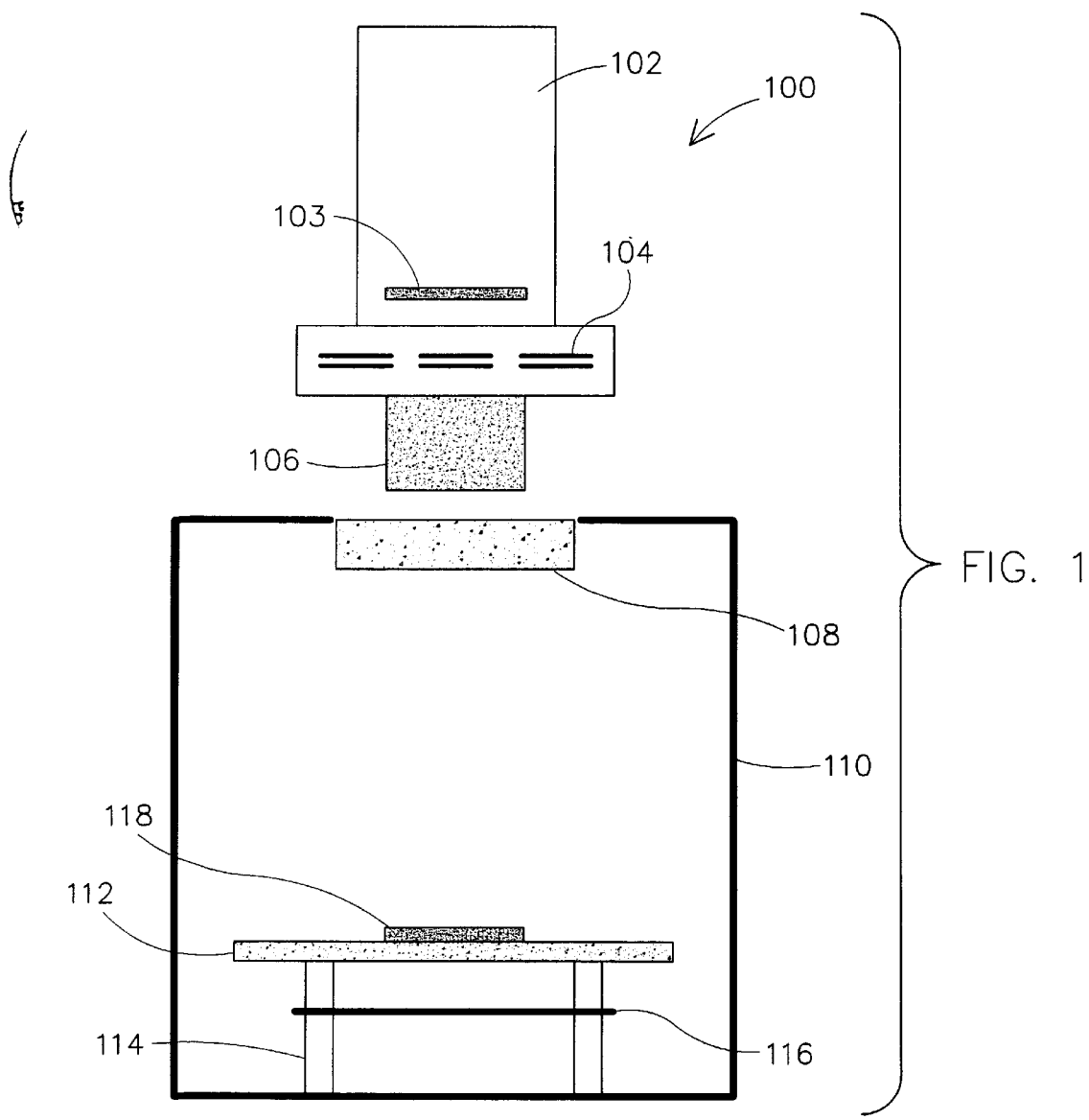
FIG. 1 shows one embodiment of an apparatus according to the present invention for parallel characterization.

The present invention finds particularly attractive application in the rapid, high throughput screening of many materials and more specifically the screening of combinatorial libraries of materials. The field of combinatorial materials science generally involves, inter alia, the synthesis of arrays of multiple different materials and the screening of such materials for useful properties. By way of illustration, without limitation, a substrate having an array of diverse materials thereon can be prepared by delivering components of materials to predefined regions on the substrate, and simultaneously reacting the components to form at least two materials. Materials which can be screened using the methods and apparatus of the present invention include, for example, covalent network solids, ionic solids and molecular solids. More particularly, materials which can be screened include inorganic materials, intermetallic materials, metal alloys, ceramic materials, organic materials, organometallic materials, non-biological organic polymers, composite materials (e.g., inorganic composites, organic composites, or combinations thereof), etc. As such, the present invention provides methods and apparatus for use in connection with the parallel analysis of novel materials having new and useful properties. Any material found to possess a useful property can be subsequently prepared on a large-scale.

Thus, as will be appreciated, an array or library of inorganic materials (e.g. alloys) on a single substrate at predefined regions thereon is provided. Such an array can consist of two or more different materials, 10 or more different materials, and preferably more than 10, $10^2$, $10^3$, $10^4$, $10^5$ or $10^6$ different materials. In some embodiments, the density of regions per unit area will be greater than 0.04 regions/cm$^2$, more preferably greater than 0.1 regions/cm$^2$, even more preferably greater than 1 region/cm$^2$, even more preferably greater than 10 regions/cm$^2$, and still more preferably greater than 100 regions/cm$^2$. In most preferred embodiments, the density of regions per unit area will be greater than 1,000 regions/cm$^2$, more preferably 10,000 regions/cm$^2$, even more preferably greater than 100,000 regions/cm$^2$, and still more preferably 10,000,000 regions/cm$^2$.

In accordance with the present invention, such materials are then screened in parallel for useful properties. More specifically, the present invention advantageously permits for rapid and high throughput screening of such arrays, allowing useful data to be generated about the materials in the array, particularly with respect to phase transition temperatures (e.g. without limitation, melting point) of such materials. Additional details about synthesis and screening of combinatorial libraries can be found, for instance, in commonly assigned, co-pending U.S. application Ser. Nos. 08/327,513; 09/156,827; and 08/841,423, each of which is incorporated herein by reference.

Changes in the electrical conductivity, surface morphology, and dielectric constant of a material generally lead to changes in the reflectance of a material. These material changes are expected to be particularly large at a phase change or transition, such as between the solid state and the liquid state. It is these large changes that form the basis for the screen of the present invention. The invention generally detects changes in the emitted power R(T) as the temperature of combinatorial library of materials is increased through the phase change (e.g. melting point) of materials in the library. Any large sudden changes in the radiation, such as the measured reflectivity or emissivity, of a particular material for a given temperature indicates a phase change for that material. In this context, a "sudden large" change would refer to, for example, a 5–10% change in the relative intensity of a material over a 50–100 ms period would indicate a phase change point. In other embodiments, the change may be more than 5% and preferably more than 10%. Also, the change may take 200 ms or more, but preferably less than 100 ms. Samples or members of a combinatorial library may be measured in parallel or sequentially using the method and apparatus of this invention, with samples being measured two at a time, 10 at a time or more, up to the number of members in the combinatorial library. Thus, the system and method can measure 2 or more samples per second, 10 or more samples per second, 50 or more samples per second and preferably 60 or more samples per second for phase point changes.

To monitor changes in the reflectivity or emissivity of a material, the spectral excitance of the material in response to heating can be detected at a single wavelength, a narrow wavelength band, or over a wide wavelength spectrum. One method is to use a detector that is sensitive to a specific single wavelength and to measure the integrated excitance (intensity) as a function of temperature. Also, experiments detecting the spectral excitance over a narrow band of wavelengths or even a wide spectrum of wavelengths result in accurate melting point measurements as well.

FIG. 1 is a schematic representation of one preferred apparatus for conducting parallel screening of phase changes. The apparatus includes a plurality of single member detectors or a position-sensitive detector (i.e., one that can correlate the specific data with a specific measured position in the array) so that an entire library of members can be measured simultaneously. Because the screen of the present invention measures members at relatively high temperatures, which provide observable infrared radiation characteristics, the detectors are preferably tuned to infrared wavelengths. However, other wavelengths (e.g., visible light wavelengths, either alone or in conjunction with infrared wavelengths) can be used for measurement as well, and those of skill in the art can select an appropriate detector for such wavelengths. Of course, the skilled artisan will recognize that the invention is not limited to the structure shown in FIG. 1, but can also encompass any other system that correlates emissivity or radiation measurements of members with temperature to obtain phase transition data. In addition, although the examples below focus on heating solid materials to determine their melting point, the invention is just as applicable for any solid or liquid member materials that are taken through one or more phase changes (e.g. crystallization, solidification, melting point, sublimation/evaporation, metal-insulator phase transitions, etc.) via heating or cooling.

As shown in FIG. 1, a preferred apparatus 100 for conducting a parallel phase change (e.g. melting point) detection includes a detector 102 (illustrated here as an infrared detector, and specifically, an infrared camera containing an infrared focal plane array (FPA) 103), preferably a filter and aperture positioning device 104, a lens 106 (e.g. camera lens), a window 108 (preferably an infrared transparent window), a vacuum chamber 110, a heater 112, optional heater supports 114, and a reflector 116 (e.g. an infrared reflector). A combinatorial library 118 having members to be screened is placed on the heater 112. The interaction and operation of these components will be described in greater detail below with respect to parallel screening. Of course, other combinations of devices can be employed to obtain observable simultaneous or near-simultaneous phase change data from the combinatorial library.

Figure 2:
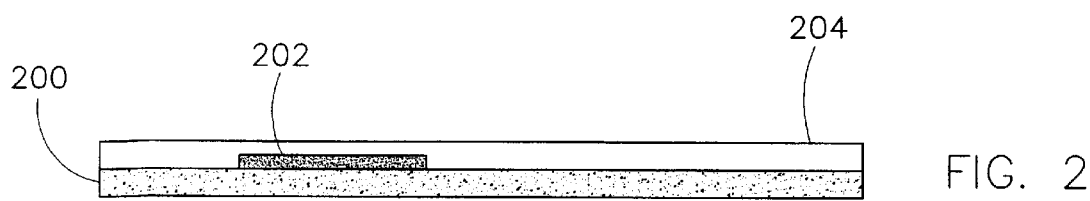
FIG. 2 shows a preferred substrate structure for supporting library members in the inventive apparatus.

Referring now to FIG. 2, a substrate 200 is preferably used to support the library members. Amorphous carbon is one example of a preferred substrate material to be used for detecting melting points of alloys in the invention because it can withstand temperatures of over 1000° C. in a vacuum environment, has good mechanical properties, and is relatively inert. Any material that has the relevant properties similar to amorphous carbon, however, can be used in the substrate 200 as well. By way of example, the substrate 200 may be selected from any of a wide variety of materials including polymers, plastics, pyrex, quartz, resins, silicon, silica or silica-based materials, carbon, metals, glasses, crystals, etc. The substrates may be organic, inorganic, biological, nonbiological or a combination. The substrate may be any suitable shape and preferably forms a rigid support. The choice of substrate will depend on the type of materials in the library, the phase transition being screened and the detector used to detect the radiation intensity change (e.g. the reflectivity or emissivity change) of the materials.

In the present preferred embodiment, the substrate 200 is used as a temperature reference throughout the melting point measurement. As shown in FIG. 2, library members 202 can be synthesized directly on the substrate. A thin capping layer 204 of a refractory material, such as $Al_2O_3$ or $Ta_2O_3$ is preferably deposited over the library members 202 to minimize evaporation of the library members as the temperature is increased. Any other suitable protective layer may likewise be employed. The capping layer 204 is preferably sufficiently thin, so that it does not adversely affect the infrared intensity measurement. To illustrate, in the present embodiment it is about 2000 angstroms. The library members 202 themselves can be deposited on the substrate using any known combinatorial technique, including the combinatorial materials science techniques identified in the aforenoted U.S. Patent Applications.

Though other methods are possible (including convective or radiation methods), with respect to heating of the library 118, one of two conductive methods preferably is used. One way is by using the substrate 200 as a resistive heater. For instance, if the substrate is amorphous carbon, this takes advantage of the electrical conductivity and the mechanical stability of the amorphous carbon and allows the library to be heated directly by passing current through the substrate. Temperatures as high as 1000° C. can be reached using this method.

Another preferred way to heat the library members is by placing the substrate on a suitable heater, such as a graphite heater. The heater should have low thermal mass because the temperature range for the experiment ramps up and back down at around 30–50° C./second between room temperature and 1300°C.; a quicker heating response provides clearer indications of the library members' phase transition (e.g. melting point) and also results in a faster experiment.

To screen the library members in parallel, the library is heated so that all members are at an elevated temperature simultaneously. A detector then reads the thermal data it observes from the substrate. The data can be stored and retrieved so that particular information about a particular material in the library can be retrieved and correlated to the specific material to yield useful information about such material.

To illustrate the context of screening a material for melting points using an infrared camera, the infrared camera 102 and lens 106, along with the infrared focal plane array (FPA) 103, is positioned over the library 118. If desired, the filter and aperture positioning device 104 can be placed in between the FPA 103 and the member library 118. As noted above, parallel detection of the melting points of a material library, according to the present invention involves using the infrared FPA 103 to monitor changes in the emissivity/reflectivity of each library member as its temperature is raised. One example of a preferred FPA is a 256×256 member array (e.g. InSb array) having a predetermined wavelength sensitivity (e.g. between about 800 nm and 5.5 $\mu$m, such as a visible-mid-infrared FPA), and that can capture images at a predetermined speed (e.g. at least 20 frames per second). Data from the FPA 103 is preferably captured in real time as the members are heated and cooled. The data is stored, reduced and analyzed in a computer using software that can obtain chemical data from images, such as software disclosed in co-pending PCT Application No. PCT/US99/07358 to entitled "Analysis of Chemical Data From Images", incorporated herein by reference. In general, the software is able to determine, from the captured images, a series of values for selected regions in the library and calculating a figure of merit, such as an emittance change as a function of temperature, a phase transition point or thermoelectric figure of merit, for a selected library member. A graphical representation of the figures of merit is optionally displayed for user analysis.

The FPA 103 can monitor the libraries over a wide wavelength range, and the present description is not intended to limit the invention. For illustration purposes, standard infrared optics that presently are commonly available are tuned to between about 3–5 $\mu$m and between about 8–14 $\mu$m. These wavelength ranges are ranges generally in the electromagnetic spectrum in which the air absorption is lowest. Thus, the actual experiment can be conducted within these narrow wavelength ranges, despite the FPA's 103 ability to detect wavelengths outside the ranges. The invention is not, however, restricted to conducting screening in the wavelength ranges tuned by standard infrared optics; phase change (e.g. melting point) detection can be conducted over any wavelength region detectable by the FPA 103. Further, as shown in FIG. 1, measuring the intensity of infrared radiation for a member at or above 1300° C. (as may be encountered with some materials) may require apertures and neutral density filters 104 to be placed between the member and the FPA 103 to avoid saturating the array.

In the context of an illustrative example screening for melting points of a metal alloy, the library 118 is placed on the heater 112 and heated using either heating method described above. In this example, the members are placed on an amorphous carbon substrate and heated by placing the substrate on the heater 112. During the heating process, the FPA 103 in the infrared camera 102 gathers reflectivity/emissivity data over time about each member as its temperature increases. This data is then correlated with temperature data, as will be explained in greater detail below, to obtain the melting point for each member. The reduced pressure in vacuum chamber 110 helps to ensure that the temperatures of the members in the library 118 are not affected by heat losses to the environment, air convection, etc.

Advantageously, the parallel screen of the present invention is capable of screening combinatorial libraries at temperatures of at least 1200° C. under vacuum conditions, with heating and cooling rates as high as about 30° C./second. Other possible temperature ranges and rates include temperatures of at least 1400° C. at about 50° C./second and at least 500° C. at about 30° C./second.

Figure 3:
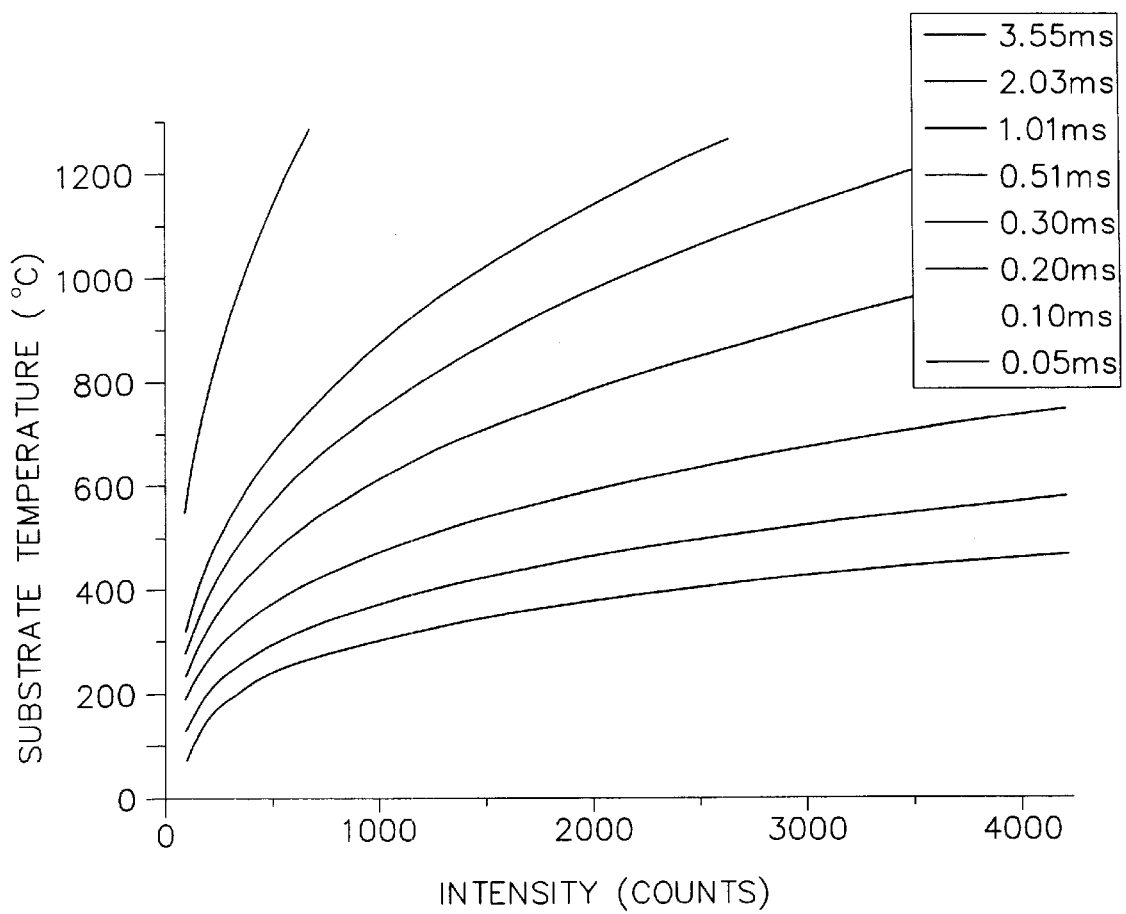
FIG. 3 is an example of a temperature vs. intensity calibration curve obtained from the inventive apparatus.

FIG. 3 is a calibration curve that links the substrate (e.g. carbon substrate) temperature of the present invention to a given measured radiation intensity at different camera integration settings (illustrated here as eight settings). As noted above, the FPA 103 records the emitted infrared intensity for the library members and for the carbon substrate as a function of time as the temperature of the library is increased. Obtaining a calibration curve linking the emitted infrared intensity from the carbon substrate to the actual temperature of the substrate, which can be determined with a measuring device such as a thermocouple, allows the substrate's radiation intensity over time to act as a reference temperature throughout the measurement. Although amorphous carbon does not have a constant emissivity as its temperature changes, the emissivity curve varies smoothly over the temperature range at which the melting point tests are conducted, as can be seen in FIG. 3. This allows changes in the substrate's emissivity to be addressed in the temperature calibration.

Figure 4:
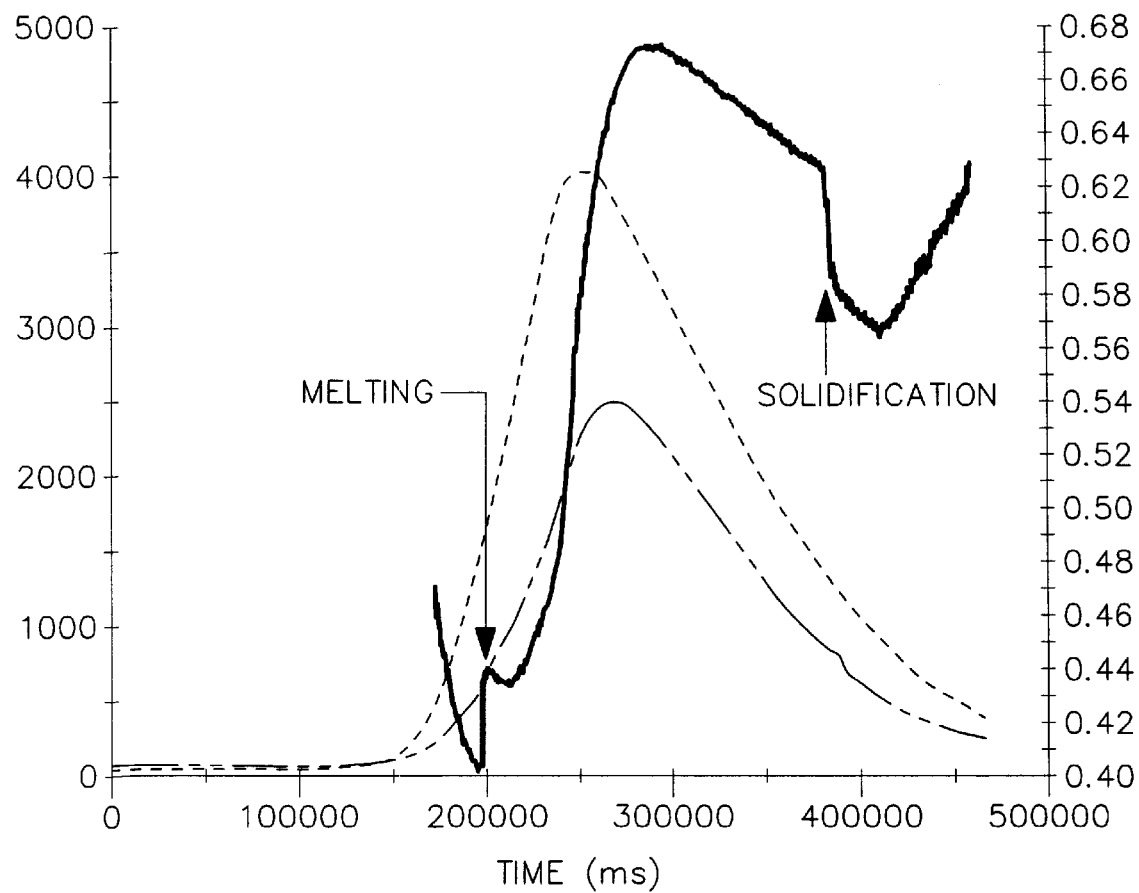
FIG. 4 is an example of intensity vs. time curves obtained via the inventive apparatus.

FIG. 4 illustrates the changes in radiation intensity versus time for a reference substrate (e.g. an amorphous carbon substrate like that employed with the library), a library member, and the ratio between the two curves. As can be seen in FIG. 4, the temperature (and therefore the radiation intensity) of the carbon initially increases, reaches a maximum, then decreases over a smooth curve. The library member also exhibits a similar curve as it heats and cools, except there is a sudden increase in the radiation when it heats and a sudden drop in radiation as it cools. These sudden changes correspond to the temperatures at which the library member changes phases, e.g. melts and solidifies, respectively. The ratio of the substrate's radiation and the library member's radiation illustrates the melting point more clearly, appearing as a relatively sharp increase and a relatively sharp decrease in the graph. The temperature at which the library member changes phase is determined by reading the radiation at the points in time at which the sudden increase or decrease in the library member radiation occurs and using the calibration curve shown in FIG. 4 to determine the corresponding substrate temperature. As a result, the phase change point for every member in the library can be determined quickly.

The inventive parallel screen is particularly suitable for screening new compounds via combinatorial materials science techniques to locate compounds having specific desired properties. For example, the library members can be arranged on a substrate in a standardized format using known combinatorial chemistry techniques. This would allow the materials to be both deposited and tested in parallel, increasing the number of members that can be tested per unit time. As a result, preparation and deposition of the library materials can be automated, if desired, further accelerating the speed at which materials can be tested.

It should be appreciated that the present invention is particularly useful for measuring data associated with phase transitions, particularly from the solid to liquid or liquid to solid phases. This makes it highly attractive for and it is useful for screening melting points of metals, semiconductors, and ceramics and their respective alloys. Of course, other material systems may be screened as well, such as plastics, biological materials, or any other material.

It should be understood that various alternatives to the embodiments of the invention described herein may be employed in practicing the invention. It is intended that the following claims define the scope of the invention and that the method and apparatus within the scope of these claims and their equivalents be covered thereby. Further, all applications and patents referenced herein are explicitly incorporated by reference.

What is claimed is:

1. A system for determining phase change points of at least ten different members in a combinatorial library, comprising:
   a substrate having said at least ten different members disposed thereon and a capping layer of a refractory material deposited over said at least ten members;
   a temperature changer for simultaneously changing the temperature of each member on the substrate for achieving at least one phase change in said at least ten members;
   a detector for simultaneously monitoring changes in radiation for each member and for generating intensity data based on the detected radiation;
   a correlator for correlating the intensity data from the detector with the temperature of each member, wherein a radiation change in the member indicates a phase change point for that member such that the temperature of the phase change point is rapidly determined for the at least ten members; and
   a vacuum chamber surrounding the substrate and the temperature changer.

2. The system of claim 1, wherein the correlator correlates the intensity data from the detector with the temperature of each member by correlating the intensity data from the detector versus time and correlating the temperature of each member versus time.

3. The system of claim 1, wherein the temperature changer changes the temperature of the substrate, the detector monitors radiation changes of the substrate and generates intensity data for the substrate based on the detected radiation, and wherein the correlator correlates the intensity data from the detector with the temperature of each member by correlating the difference between the intensity data for each member and the intensity data for the substrate versus time and the intensity data for the substrate versus temperature.

4. The system of claim 3, wherein the correlator correlates the intensity of the member with temperature by:
   determining a calibration curve correlating the radiation intensity of the substrate and the temperature of the substrate;
   measuring the radiation intensity versus time of each member and the substrate; and
   calculating the ratio between the radiation intensity versus time of each member and the radiation intensity versus time of the substrate, wherein a change in the ratio for one of said members indicates the phase change point of that member.

5. The system of claim 4, wherein the system determines phase change points at a rate of at least 60 samples/second.

6. The system of claim 1, wherein the system characterizes said at least ten members in a parallel fashion.

7. The system of claim 1, wherein the system characterizes said at least ten members in a rapid serial fashion.

8. The system of claim 1, wherein the substrate is made of amorphous carbon.

9. The system of claim 1, wherein the temperature changer is a substrate heater that heats the substrate, which in turn heats said at least ten members.

10. The system of claim 9, wherein the substrate heater is a low thermal mass heater.

11. The system of claim 9, wherein the heater is a graphite heater.

12. The system of claim 9, wherein the heater is a current source that applies current through at least one of the substrate and said at least ten members to heat the members.

13. The system of claim 1, wherein the detector is a position sensitive detector.

14. The system of claim 1, wherein the detector is a plurality of single member detectors.

15. The system of claim 1, wherein the detector is a focal plane array.

16. The system of claim 15, wherein the focal plane array is a visible-mid-infrared focal plane array.

17. A system for determining phase change points of at least ten different members in a combinatorial library, comprising:
   a substrate having said at least ten different members disposed thereon;
   a temperature changer for changing the temperature of each member on the substrate;
   a detector for monitoring changes in radiation for each member and for generating intensity data based on the detected radiation;
   a computerized correlator for correlating the intensity data from the detector with the temperature of each member, wherein a radiation change in the member indicates a phase change point for that member such that the temperature of the phase change point is determined for the at least ten members within about one second of each other; and
   an environmental controller associated with the substrate and the temperature changer wherein the environmental controller is capable of adjusting an environment surrounding the at least ten members in a manner that reduces heat loss of the at least ten members to the environment.

18. The system of claim 17 wherein the correlator correlates the intensity data from the detector with the temperature of each member by correlating the intensity data from the detector versus time and correlating the temperature of each member versus time.

19. The system of claim 17 wherein the temperature changer changes the temperature of the substrate, the detector monitors radiation changes of the substrate and generates intensity data for the substrate based on the detected radiation, and wherein the correlator correlates the intensity data from the detector with the temperature of each member by correlating the difference between the intensity data for each member and the intensity data for the substrate versus time and the intensity data for the substrate versus temperature.

20. The system of claim 19, wherein the correlator correlates the intensity of the member with temperature by:
   determining a calibration curve correlating the radiation intensity of the substrate and the temperature of the substrate;
   measuring the radiation intensity versus time of each member and the substrate; and
   calculating the ratio between the radiation intensity versus time of each member and the radiation intensity versus time of the substrate, wherein a change in the ratio for one of said members indicates the phase change point of that member.

21. The system of claim 17, wherein the system characterizes said at least ten members in a parallel fashion.

22. The system of claim 17, wherein the system characterizes said at least ten members in a rapid serial fashion.

23. The system of claim 17, wherein the system determines phase change points at a rate of at least 60 samples/second.

24. The system of claim 17, wherein the substrate is made of amorphous carbon.

25. The system of claim 17, further comprising a capping layer deposited on top of said at least ten members on the substrate.

26. The system of claim 17, wherein the temperature changer is a substrate heater that heats the substrate, which in turn heats said at least ten members.

27. The system of claim 26, wherein the substrate heater is a low thermal mass heater.

28. The system of claim 26, wherein the heater is a graphite heater.

29. The system of claim 26, wherein the heater is a current source that applies current through at least one of the substrate and said at least ten members to heat the members.

30. The system of claim 17, wherein the detector is a position sensitive detector.

31. The system of claim 17, wherein the detector is a plurality of single member detectors.

32. The system of claim 17, wherein the detector is a focal plane array.

33. The system of claim 32, wherein the focal plane array is a visible-mid infrared focal plane array.

34. A system for determining melting points of at least ten different members in a combinatorial library, comprising:

- a conductive substrate having the at least ten different members disposed thereon and a capping layer of a refractory material deposited over said at least ten members, wherein the substrate is at least partially formed of an amorphous carbon;
- a low thermal mass heater that ramps up and down at a rate of around 30–50° C. per second between room temperature and 1300° C. and that supports the substrate and is adapted for simultaneously heating the at least ten members.
- a vacuum chamber surrounding the substrate, the at least ten members, and the heater;
- an infrared camera positioned over the substrate and the at least ten members, the infrared camera having a focal plane array for monitoring changes in radiation of the at least ten members over time as they are heated by the heater and generating image data; and
- a computer that obtains the image data from the focal plane array and correlates the radiation intensities of the at least ten members with temperature, wherein a radiation change in the member indicates a melting point for that member such that the temperature of the melting point is determined for the at least ten members within about one second of each other.

35. The system of claim 34, wherein the focal plane array is a visible-mid-infrared focal plane array.

36. The system of claim 34, wherein the computer correlates the intensity of the member with temperature by:

- determining a calibration curve correlating a radiation intensity of the substrate and the temperature of the substrate;
- measuring the radiation intensity versus time of each of the members and the substrate; and
- calculating the ratio between the radiation intensity versus time of each of the members and the radiation intensity versus time of the substrate, wherein a change in the ratio for a given member indicates the melting point of that member.

37. The system of claim 34, wherein the system characterizes said members in a parallel fashion.

38. The system of claim 34, wherein the system characterizes said members in a rapid serial fashion.

39. The system of claim 34, wherein the system determines phase change points at a rate of at least 60 samples/second.

40. The system of claim 34, wherein the substrate is made of amorphous carbon.

41. The system of claim 34, wherein the heater heats the substrate, which in turn heats said members.

42. The system of claim 34, wherein the heater is a graphite heater.

43. The system of claim 42, wherein the heater is a current source that applies current through the substrate to heat the members.

44. The system of claim 34, wherein the camera is position sensitive.

* * * * *

UNITED STATES PATENT AND TRADEMARK OFFICE
CERTIFICATE OF CORRECTION

PATENT NO.   : 6,536,944 B1
DATED        : March 25, 2003
INVENTOR(S)  : Archibald et al.

It is certified that error appears in the above-identified patent and that said Letters Patent is hereby corrected as shown below:

<u>Column 9,</u>
Line 40, the period after the word "members" should be replaced with a semi-colon Signed and Sealed this Seventeenth Day of June, 2003

JAMES E. ROGAN
*Director of the United States Patent and Trademark Office*